US012685594B2

(12) United States Patent
Poland

(10) Patent No.: US 12,685,594 B2
(45) Date of Patent: Jul. 21, 2026

(54) ULTRASOUND OBJECT POINT TRACKING

(71) Applicant: KONINKLIJKE PHILIPS N.V., Eindhoven (NL)

(72) Inventor: Mckee Dunn Poland, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 111 days.

(21) Appl. No.: 17/629,430

(22) PCT Filed: Jul. 23, 2020

(86) PCT No.: PCT/EP2020/070893
§ 371 (c)(1),
(2) Date: Jan. 24, 2022

(87) PCT Pub. No.: WO2021/013971
PCT Pub. Date: Jan. 28, 2021

(65) Prior Publication Data
US 2022/0241024 A1      Aug. 4, 2022

Related U.S. Application Data

(60) Provisional application No. 62/878,103, filed on Jul. 24, 2019.

(30) Foreign Application Priority Data

Oct. 10, 2019    (EP) ..................................... 19202472

(51) Int. Cl.
*A61B 34/20*        (2016.01)
*A61B 8/00*         (2006.01)
(Continued)

(52) U.S. Cl.
CPC ............ *A61B 34/20* (2016.02); *A61B 8/0841* (2013.01); *A61B 8/12* (2013.01); *A61B 8/463* (2013.01); *A61B 2034/2063* (2016.02)

(58) Field of Classification Search
CPC ...... A61B 2034/2063; A61B 2090/378; A61B 2090/3786; A61B 2090/3929; A61B 34/20; A61B 8/0841; A61B 8/12; A61B 8/463
See application file for complete search history.

(56) References Cited

U.S. PATENT DOCUMENTS

2006/0241451 A1*  10/2006  Nakaya .................. A61B 8/463
                                                    600/443
2014/0296694 A1   10/2014  Jaworski
(Continued)

FOREIGN PATENT DOCUMENTS

WO        2018149887 A1     8/2018
WO        2019070729 A1     4/2019

OTHER PUBLICATIONS

International Search Report and Written Opinion of PCT/EP2020/070893, dated Oct. 5, 2020.

*Primary Examiner* — Michael J Carey
*Assistant Examiner* — Maria Christina Talty

(57) ABSTRACT

An ultrasound device is provided for imaging an anatomical region. The ultrasound device includes an ultrasound probe (288). The ultrasound device further includes a medical instrument (202) having an ultrasound transducer (279) mounted thereto. The ultrasound device also includes a hardware processor (214) configured to render a Region Of Interest (ROI) relative to a distal end of the medical instrument on an ultrasound image displayed on a display device, and selectively perform a dynamic ROI refinement as the medical instrument is moved through the anatomical region to increase a location precision of the distal end of the
(Continued)

medical instrument in the ultrasound image. The dynamic ROI refinement is generated in accordance with physical characteristics of the medical instrument and a recorded path of movement of the medical instrument through the anatomical region determined based on acoustic pulses transmitted between the ultrasound probe (288) and the ultrasound transducer (279).

17 Claims, 7 Drawing Sheets

(51) Int. Cl.
    *A61B 8/08*           (2006.01)
    *A61B 8/12*           (2006.01)

(56)            References Cited

U.S. PATENT DOCUMENTS

| | | | |
|---|---|---|---|
| 2016/0317119 A1 | 11/2016 | Tahmasebi Maraghoosh | |
| 2016/0324501 A1* | 11/2016 | Vignon | A61B 8/0841 |
| 2017/0095226 A1* | 4/2017 | Tanaka | A61B 8/4416 |
| 2017/0172539 A1 | 6/2017 | Vignon | |
| 2017/0301088 A1* | 10/2017 | Bharat | A61B 34/20 |
| 2018/0303463 A1* | 10/2018 | Zanin | A61B 8/0841 |
| 2019/0142520 A1* | 5/2019 | VanDyken | A61B 34/20 |
| | | | 606/1 |
| 2020/0037983 A1 | 2/2020 | Poland | |

* cited by examiner

ULTRASOUND OBJECT POINT TRACKING

CROSS-REFERENCE TO PRIOR APPLICATIONS

This application is the U.S. National Phase application under 35 U.S.C. § 371 of International Application No. PCT/EP2020/070893, filed on Jul. 23, 2020, which claims the benefit of U.S. Provisional Patent Application Ser. No. 62/878,103, filed Jul. 24, 2019 and European Patent Application No. 19202472.7, filed on Oct. 10, 2019. These applications are hereby incorporated by reference herein.

BACKGROUND OF THE INVENTION

Technical Field

This disclosure relates to object detection and more particularly to ultrasound object point tracking.

Description of the Related Art

Ultrasound permits the internal imaging of organs. Medical devices used during procedures can also be imaged with ultrasound. However, accurately pinpointing medical instruments during ultrasound procedures is challenging.

As such, there is a need for accurate ultrasound object point tracking.

SUMMARY OF THE INVENTION

According to an aspect of the present invention, an ultrasound device is provided for imaging an anatomical region. The ultrasound device includes an ultrasound probe. The ultrasound device further includes a medical instrument having an ultrasound transducer mounted thereto. The ultrasound device also includes a hardware processor configured to render a Region Of Interest (ROI) relative to a distal end, for example a tip, of the medical instrument on an ultrasound image displayed on a display device, and selectively perform a dynamic ROI refinement as the medical instrument is moved through the anatomical region to increase a location precision of the distal end of the medical instrument in the ultrasound image. The dynamic ROI refinement is generated in accordance with physical characteristics of the medical instrument and a recorded path of movement of the medical instrument through the anatomical region determined using the ultrasound probe.

According to another aspect of the present invention, an ultrasound system is provided for imaging an anatomical region. The ultrasound system includes an ultrasound probe. The ultrasound system further includes a medical instrument having an ultrasound transducer mounted thereon. The ultrasound system also includes a display configured to display a position of the medical instrument by rendering a Region Of Interest (ROI) relative to a distal end of the medical instrument on an ultrasound image. The ultrasound system additionally includes a hardware processor configured to track the medical instrument in the anatomical region based on acoustic pulses transmitted between the ultrasound probe and the ultrasound transducer, and selectively perform a dynamic ROI refinement as the medical instrument is moved through the anatomical region to increase a location precision of the distal end of the medical instrument in the ultrasound image. The dynamic ROI refinement is generated in accordance with physical characteristics of the medical instrument and a recorded path of movement of the medical instrument through the anatomical region determined using the ultrasound probe.

According to yet another aspect of the present invention, in an ultrasound system that tracks a medical instrument in an anatomical region using an ultrasound transducer mounted on the medical instrument and displays a position of the medical instrument by rendering a Region Of Interest (ROI) relative to the distal end on an ultrasound image displayed on a display device, a method is provided. The method includes selectively performing a dynamic ROI refinement as the medical instrument is moved through the anatomical region to increase a location precision of the distal end of the medical instrument in the ultrasound image. The dynamic ROI refinement is generated in accordance with physical characteristics of the medical instrument and a recorded path of movement of the medical instrument through the anatomical region.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Embodiments of the present invention are directed to ultrasound object point tracking. The present invention reduces the ROI shape (e.g., circle, triangle, square, etc.) size and moves the ROI shape closer to the object tip so that the confidence of the tip location is critically increased. In an embodiment, the object can be a needle such as a regional anesthesia needle or a biopsy needle. Of course, other objects can also be used, with some illustrative examples being described herein.

In one embodiment, an ultrasound system has a subsystem that tracks an object in tissue by an ultrasound transducer mounted on or near the tip of the object, and further has a display which shows the position of the object by rendering a ROI on the ultrasound image. In an embodiment, an apparatus is provided for refining the ROI dynamically as the object is moved through tissue to increase precision and correct for location discrepancies. The refinement is generated in accordance with physical characteristics of the object and the recorded path of movement of the object through the tissue.

In an embodiment, the refinement can involve shrinking the ROI shape so that the size of the ROI shape more accurately represents a confident location of the object than before the path of movement is recorded and the refinement is implemented.

In an embodiment, the refinement can involve advancing the ROI shape so that the position of the ROI shape more accurately represents the edge of interest of the object than before the path of movement is recorded and the refinement is implemented.

In an embodiment, the refinement can be made relative to a specialized needle used for regional anesthesia. Of course, the refinement can be made relative to other medical devices than needles.

Figure 1:
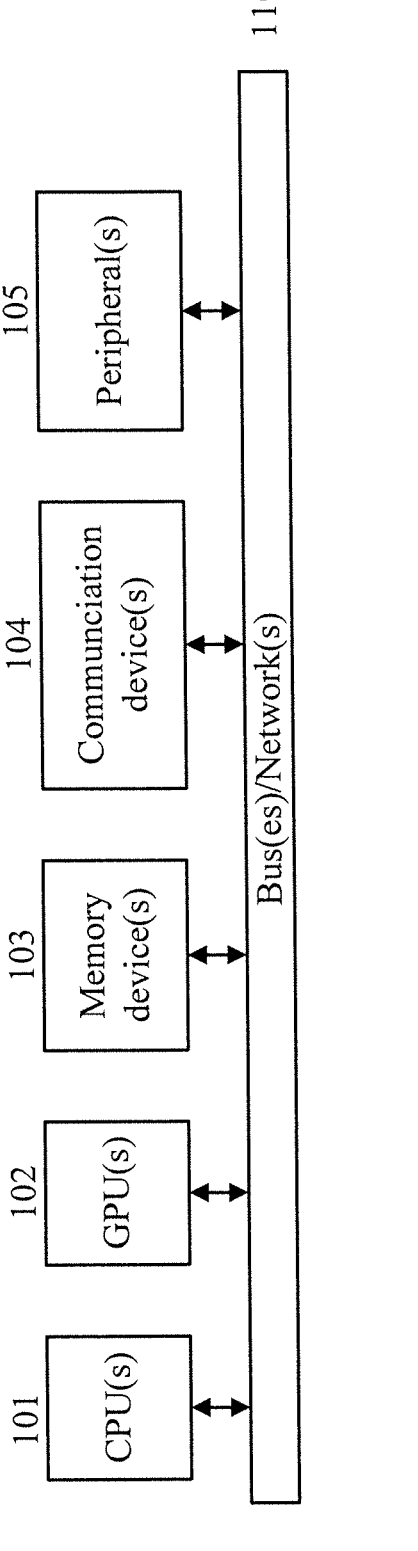
FIG. 1 is a block diagram showing an exemplary processing system, in accordance with an embodiment of the present invention.

FIG. 1 is a block diagram showing an exemplary processing system 100 to which aspects of the present invention may be applied. The processing system 100 includes a set of processing units (e.g., CPUs) 101, a set of GPUs 102, a set of memory devices 103, a set of communication devices 104, and set of peripherals 105. The CPUs 101 can be single or multi-core CPUs. The GPUs 102 can be single or multi-core GPUs. The one or more memory devices 103 can include caches, RAMs, ROMs, and other memories (flash, optical, magnetic, etc.). The communication devices 104 can include wireless and/or wired communication devices (e.g., network (e.g., WIFI, etc.) adapters, etc.). The peripherals 105 can include a display device, a user input device, a printer, an imaging device, and so forth. Elements of processing system 100 are connected by one or more buses or networks (collectively denoted by the figure reference numeral 110).

In an embodiment, memory devices 103 can store specially programmed software modules to transform the computer processing system into a special purpose computer configured to implement various aspects of the present invention. In an embodiment, special purpose hardware (e.g., Application Specific Integrated Circuits, and so forth) can be used to implement various aspects of the present invention.

Of course, the processing system 100 may also include other elements (not shown), as well as omit certain elements. For example, various other input devices and/or output devices can be included in processing system 100, depending upon the particular implementation of the same. For example, various types of wireless and/or wired input and/or output devices can be used. Moreover, additional processors, controllers, memories, and so forth, in various configurations can also be utilized. These and other variations are contemplated given the present teachings.

Moreover, it is to be appreciated that various figures as described below with respect to various elements and steps relating to aspects of the present invention that may be implemented, in whole or in part, by one or more of the elements of system 100.

Computer processing system 100 can be part of an ultrasound system implementing one or more aspects of the present invention.

A further description will now be given regarding various aspects of the present invention. In sum, the present invention can both shrink a ROI shape and advance the ROI shape by a distance value D.

The value D can be determined using two components.

A first component for determining the value D is embedded firmware in the pulse detection hardware. The embedded firmware component performs a linear regression on the series of needle location points detected, and determines the trajectory slope. The embedded firmware component then applies logic to determine the distance D, based on the trajectory and regression statistics. The embedded firmware sends D to the system along with the object tracking location coordinates.

A second component for determining the value D is system software at the rendering stage, which locates and draws the ROI on the live image. The system software takes the value of D and uses it to reduce and advance color the ROI shape as determined by the magnitude of D and the dimensions of the displayed image.

Of course, other implementations of the two preceding elements and their functionality can be used.

When active, the present invention both advances the rendered circle by a calculated distance D in the forward direction of needle tip movement and simultaneously reduces the radius of the circle by the exact same distance D. Thus, the leading edge point of the circle is unchanged, but the circle more closely surrounds the needle tip. The radius reduction/displacement D is qualified by an active slope value, and only if the Y component of the path direction is near zero or negative (e.g., tip going deeper) is the radius reduction/displacement D implemented.

Essentially, the maximum magnitude of D is the constant known distance between the needle transducer and the tip of the needle, determined by the needle manufacturing process. An illustrative value can be 3 mm. Of course, other values can be used. The angle of advance of the ROI shape is the regressed slope output. The advance is thus a simple extrapolation of the needle path from the ultrasound transducer to the needle tip along the structure of the needle shaft. The extrapolation correctly presumes that the path of insertion is substantially linear, which will be true for not only a needle, but also for other tracked objects. Once the present invention has sufficient slope and regression state to perform its correction, the actual magnitude of D is smoothly ramped from zero (no ROI change) to a maximum across a series of rendered frames, and when D is non-zero, the color of the ROI shape or some other visually perceptible parameter of the ROI shape (type of line used, thickness of line used, etc.) can be changed to indicate that the present invention is refining the ROI position.

The action is controlled by parameters which control smoothing the behavior across frames and which limit the amount of reduction/displacement D, so that the rendered circle is still useful, accurate, and pleasing. In the case of withdrawing the needle (positive Y slope) or in the unusual case of inserting the needle through tissue but towards the probe face (again positive Y slope), the present invention is benignly de-activated.

Once a valid path slope with negative Y activates the present invention, the smaller circle rendering will be retained, even if the needle momentarily halts its advance.

In the unusual case of insertion approaching the probe face, withdrawing the needle will result in the reduced circle improperly retreating behind the needle tip. For that reason, the refined ROI feature should be enabled by a User Interface (UI) button, so that the clinician can choose to bypass the refined ROI feature for unusual cases. Regardless, the behavior would generally be benign because the needle is being withdrawn.

The present invention is very simple in that it does not rely at all on image processing for needle shaft detection, and need not involve complex probe attitude sensing (a gyro data stream).

Figure 2:
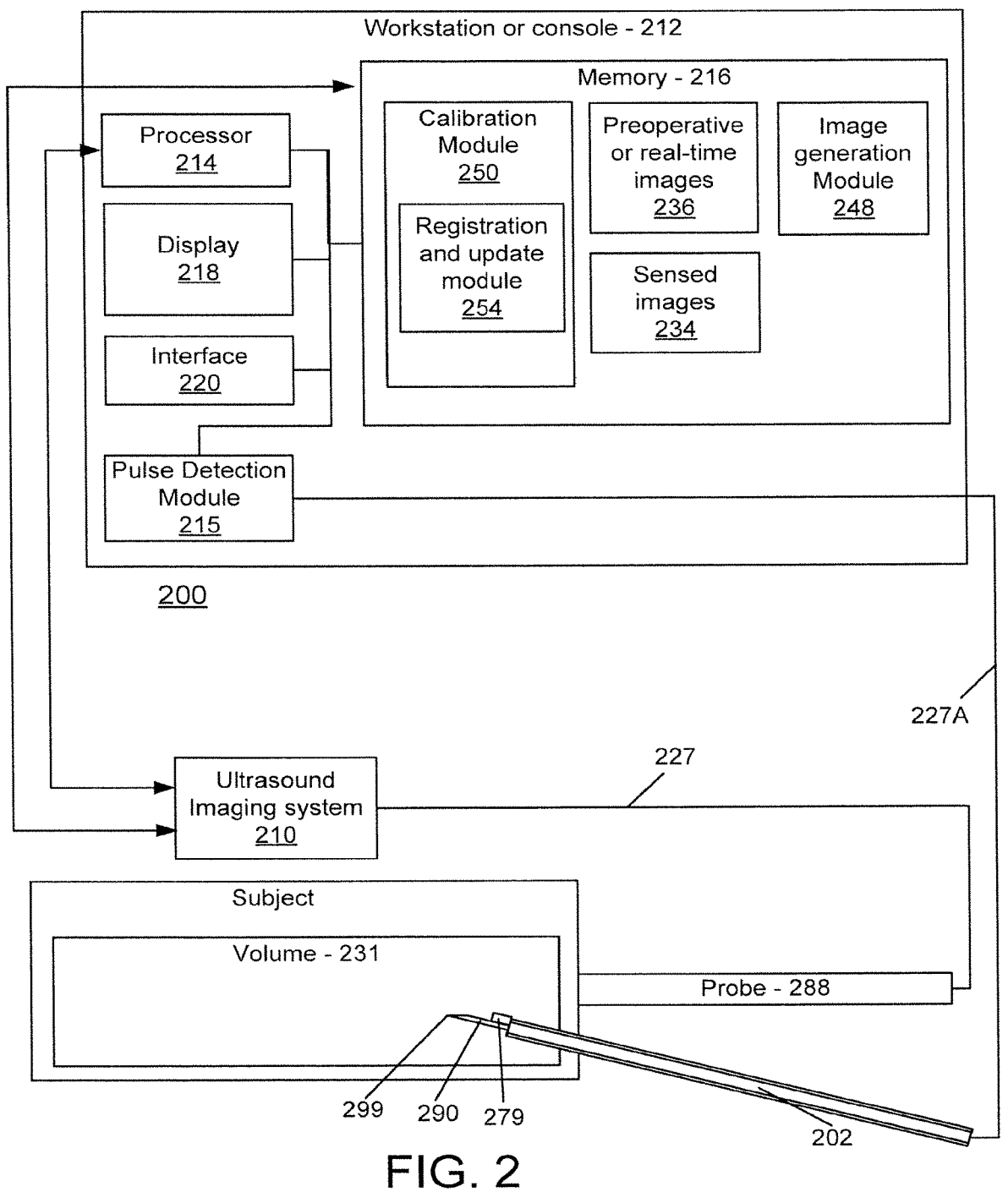
FIG. 2 is a block diagram showing an ultrasound system which employs a distal end configuration, in accordance with an embodiment of the present invention.

FIG. 2 is a block diagram showing an ultrasound system 200 which employs a tip configuration, in accordance with an embodiment of the present invention.

System 200 may include a workstation or console (hereinafter "workstation") 212 from which a procedure is supervised and/or managed. In an embodiment, one or more elements of system 200 can be implemented by computer processing system 100 of FIG. 1. Workstation 212 preferably includes one or more processors 214 and memory 216 for storing programs and applications. In particular, the memory 216 includes a calibration module 250 (in turn, including a registration and update module 254), pre-operative or real time images 236, an image generation module 248, and sensed images 234.

System 200 includes other elements such as a display 218, an interface 220, a pulse detection module 215, an ultrasound imaging system 210, an ultrasound probe 288, and a medical or interventional device (hereinafter medical device) 202. Various elements of system 200, such as, but not limited to, pulse detection module 215, can have its own memory and controller, depending upon the implementation.

The pulse detection module 215 interprets ultrasound feedback signals from ultrasound probe 288 and an ultrasound transducer 279 mounted on medical device 202.

Pulse detection module 215 can use ultrasound signal feedback (and/or any other feedback) to reconstruct changes in position associated with a medical device 202 in its surrounding region (e.g., volume 231) relative to the ultrasound probe 288, by means of analyzing signals from transducer 279 mounted on the medical device 202 as described further below.

The medical device 202 may include a catheter, a guidewire, an endoscope, a robot, an electrode, a filter device, a balloon device, a needle, or other medical component, etc. The preceding devices are merely illustrative and, thus, other devices can also be used with medical device 202. For the sake of illustration, medical device 202 includes a needle having a distal end, i.e. tip 299. The ultrasound transducer 279 is mounted on or proximate to the needle. Another medical device 202 such as, for example, a catheter, would also have the ultrasound transducer 279 mounted on the catheter. The ultrasound transducer 279 could be mounted on different positions of the medical device 202, depending upon the particular implementation.

The ultrasound probe 288 generates ultrasound signals which are reflected by structures in a patient's body in order to reproduce the structures in image form on ultrasound image system 210.

The ultrasound transducer 279 is preferably a sensor and preferably operates in a receive-only mode. In particular, the ultrasound transducer 279 receives acoustic pulse signals from ultrasound probe 288 as it performs ultrasound transmit pulse generation and received echo beamforming. The resulting acoustic transmit-receive scan lines provide the acoustic signals utilized by the ultrasound imaging system 210 to generate image data to be rendered and displayed on the ultrasound imaging system 210, the workstation 212, or both. The ultrasound transducer 279 also receives acoustic pulses from the scan lines generated by probe 288, and sends the resulting receive signals to pulse detection module 215, where it thereby calculates the position of the ultrasound transducer 279, and thus of medical device 202 (and in this example, its needle tip 299), with respect to ultrasound probe 288, and thus with respect to the image of the volume 231 that is being imaged by ultrasound probe 288. Calculating the position of ultrasound transducer 279 may include i) determining, from the ultrasound beams transmitted by ultrasound probe 288, a beam in which a maximum magnitude acoustic signal is detected by ultrasound transducer 279, and ii) determining a time of flight of the maximum magnitude acoustic signal between ultrasound probe 288 and ultrasound transducer 279. The angular position and the range of ultrasound transducer 279 respective ultrasound probe 288 may thus be determined respectively, this being based on acoustic signals transmitted between ultrasound probe 288 and ultrasound transducer 279. Furthermore, the pulse detection module 215 may reconstruct a path of position changes of ultrasound transducer 279, and thus of medical device 202 (and in this example, its needle tip 299), as mentioned previously. In another configuration ultrasound transducer 279 may be an ultrasound emitter and the position of ultrasound transducer 279 may again be determined based on acoustic signals transmitted between ultrasound probe 288 and ultrasound transducer 279. In this configuration, ultrasound pulses emitted by ultrasound transducer 279 are detected by ultrasound probe 288 and the position of ultrasound transducer 279 is determined respective ultrasound probe 288 via received echo beamforming. Received echo beamforming is the procedure via which an ultrasound image is generated. The acoustic pulses emitted by ultrasound transducer 279 are thus detected in the ultrasound images generated by ultrasound probe 288 as a bright spot in a position corresponding to the positon of ultrasound transducer 279 respective ultrasound probe 288.

Ultrasound probe 288 is connected to the workstation 212 through cabling 227, via the ultrasound imaging system 210. Medical device 202 is connected to pulse detection module 215 through cabling 227A. The cabling 227 and/or 227A may include fiber optics, electrical connections, other instrumentation, and so forth, as needed.

In one embodiment, workstation 212 includes an image generation module 248 configured to receive feedback from the ultrasound probe 288 and record accumulated position data as to where the medical device 202 has been within the volume 231. The ultrasound imaging system 210 is a source of images 236 upon which the overlap of the needle (or whatever tracked medical device 202) tip location ROI is placed. A series of sensed images 234 of a history 236 of the ultrasound probe 288 within the space or volume 231 can also be displayed on a display device 218. Workstation 212 includes the display device 218 for viewing internal images of a subject (patient) or volume 231 and may include the sensed images 234 as an overlay or other rendering of the history 236 of visited positions of the medical device 202 in addition to the current displayed position of the device. Display 218 may also permit a user to interact with the workstation 212 and its components and functions, or any other element within the system 200. This is further facilitated by an interface 220 which may include a keyboard, mouse, a joystick, a haptic device, or any other peripheral or control to permit user feedback from and interaction with the workstation 212.

The ultrasound probe 288 is connected to the ultrasound imaging system 210 which among other things acts a source of ultrasonic pulses (e.g., a pulse generator) in conjunction with ultrasound probe 288. The imaging system and ultrasound probe 288 work together to generate acoustic scan lines, including transmit and receive phases, typically including phased array beamforming techniques to form beams which acoustically interrogate volume 231 (or a locus of scan lines therein) to collect echo data for the formation of images 236 as a series of acoustic frames. In the process of transmitting acoustic pulses for scan lines, probe 288 insonicates the region in volume 231 where medical device 202 is located, and thus also insonicates ultrasound transducer 279. Signals detected by transducer 279 are sent to pulse detection module 215 which, in conjunction with timing information from ultrasound imaging system 210, may determine the location of the tip of medical device 202 in the field of view imaged by probe 288.

In an embodiment, a needle is mounted at a distal end of the medical device 202, for example, at the tip 299 thereof. Again, other devices can be used in place of a needle as medical device 202. In such a case, ultrasound transducer 279 may be located at a different location than it would on a needle. The ultrasound transducer 279 mounted on or proximate to the needle 290 or other device detects the location of the tip 299 of the needle or other device and provides tip location information to the workstation 212. The processor 214 may be used to generate a Region of Interest (ROI) circle. According to a non-refined state, the ROI shape is centered around a center of the ultrasound transducer 279. According to aspects of the present invention, the ROI shape is changed so as to be centered around the tip 299 to better represent the position of the tip 299 as described herein.

As described above, system 200 measures and analyzes acoustic pulses observed by the needle using components such as pulse detection module 215, and by timing the acoustic pulses with respect to the timing of the scan lines in the ultrasound probe's 288 acoustic frame, and placing the location of the ultrasound transducer both in azimuth and depth on the rendered image. Thus, the position of the ultrasound transducer respective to the ultrasound probe 288 is determined based on ultrasound signals detected by the ultrasound transducer 279 on the needle.

Thus, for the sake of illustration, the medical device 202 is described as a needle. If the clinical application is regional anesthesia, anesthetic is pumped through a cannula of the needle to surround a nerve bundle, and then the needle is withdrawn and a procedure can be done by a qualified medical person. The exact location of the needle tip as seen in the ultrasound image is critical for effectiveness and safety.

On the other hand, if the clinical application is, for example, insertion of a catheter, such as for minimally invasive surgical intervention, then the needle's function is to create the puncture, lead a guide wire into a vessel, get withdrawn, and then the catheter itself is pushed into the vessel using the guide wire. In that case, the catheter that would have the ultrasound transducer 279 mounted on it, instead of (or in addition to) the needle.

These and other medical devices 202 to which the present invention can be applied are readily determined given the teachings relating to various embodiments of the present invention described herein.

While display 218 and ultrasound imaging device 210 are described herein for functions relating to displaying images, in other embodiments, a single display device can be used. For example, in an embodiment, the display 218 can be omitted, and the ultrasound imaging system 210 can provide ultrasound probe signal generation (pulse transmit), reception (pulse receive), signal demodulation and detection, filtering, and so forth, implementing a standard ultrasound signal path. The resulting detected, filtered signal stream goes into scan conversion, Doppler detection, rendering, and so forth and can be displayed within the same "system". In an embodiment, the ultrasound probe can just be a mechanical housing with some simple circuitry to drive the (typically piezoelectric) transducer elements, e.g., 128 of them. In an embodiment (e.g., system 700 of FIG. 7)), most of ultrasound the signal path (without the display) can be located in the ultrasound probe handle itself to provide a compact system.

These and other variations of system 200 are readily determined given the teachings relating to various embodiments of the present invention described herein.

Figure 3:
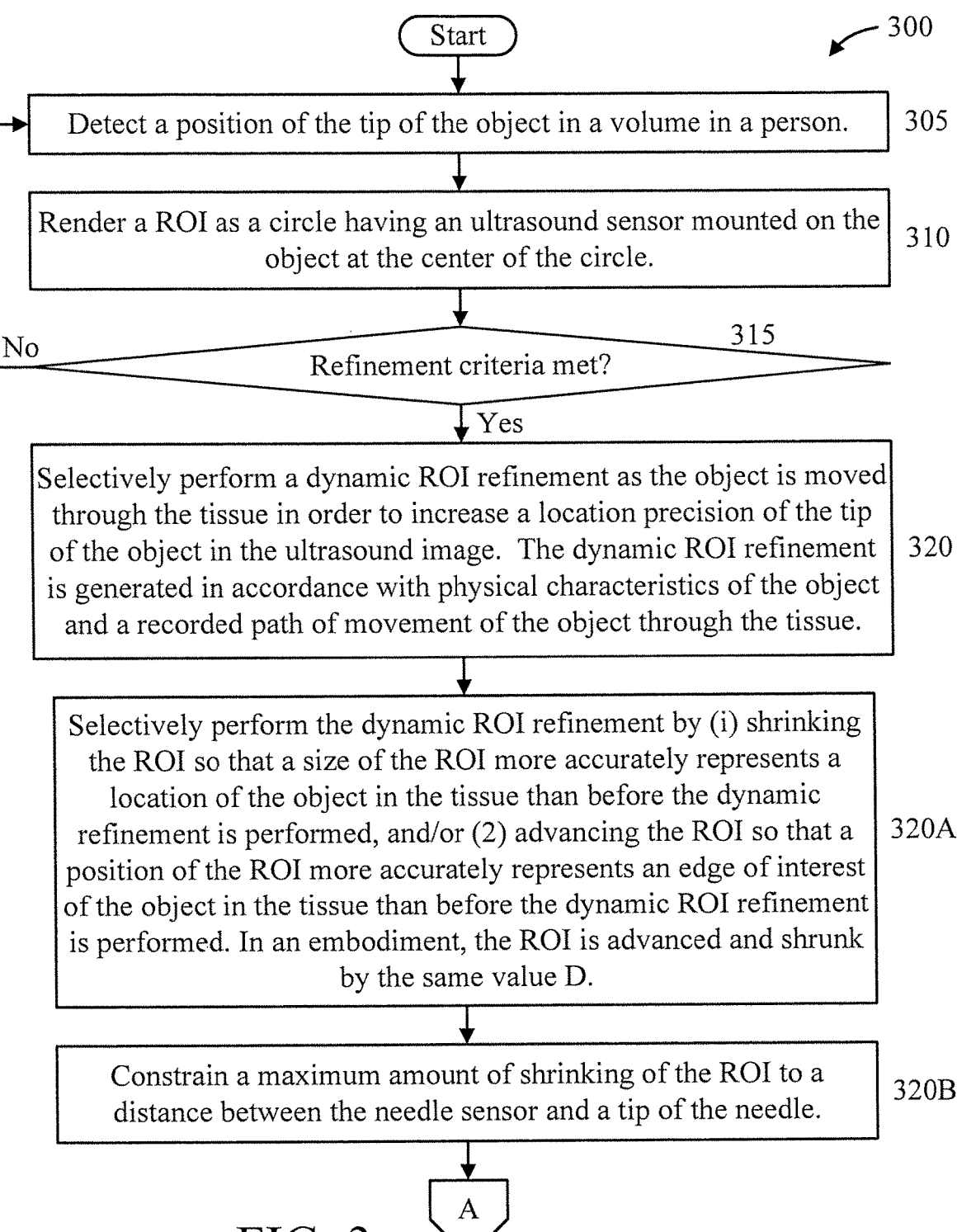
FIGS. 3-4 are flow diagrams showing an exemplary method for ultrasound object point tracking, in accordance with an embodiment of the present invention.
Figure 4:
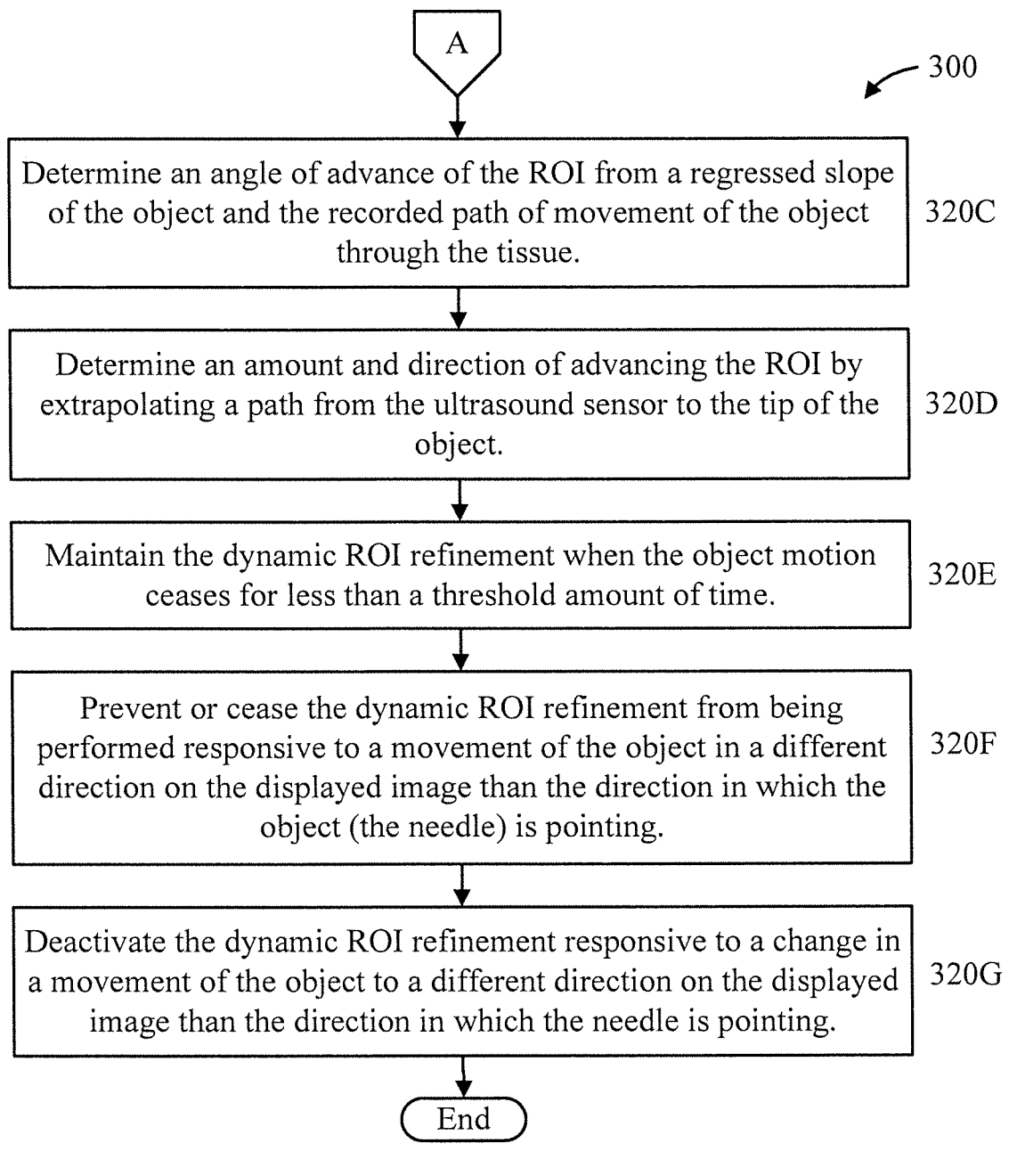

FIGS. 3-4 are flow diagrams showing an exemplary method 300 for ultrasound object point tracking, in accordance with an embodiment of the present invention. The method 300 is performed in an ultrasound system that tracks an object (e.g., an anesthesia needle) in a tissue using an ultrasound transducer mounted on or near a tip of the object and displays a position of the object by rendering a Region Of Interest (ROI) relative to the tip on an ultrasound image displayed on a display device.

At block 305, detect a position of the tip of the object in a volume in a person.

At block 310, render a ROI as a circle having an ultrasound transducer mounted on the object at the center of the circle.

At block 315, determine if refinement criteria have been met. If so, then proceed to block 320. Otherwise, return to block 305.

At block 320, selectively perform a dynamic ROI refinement of the ROI as the object is moved through the tissue to increase a location precision of the tip of the object in the ultrasound image. The dynamic ROI refinement is generated in accordance with physical characteristics of the object and a recorded path of movement of the object through the tissue. The phrase "increasing a location precision" refers to more precisely locating the ROI shape (e.g., circle) with respect to a particular location of the object such as the tip of a needle. The location precision can be made more precise, for example, by moving a center of the shape (e.g., circle) to the tip of the needle (versus centered over the ultrasound transducer) and shrinking an overall diameter or size of the shape.

In an embodiment, the dynamic ROI refinement is only performed responsive to a movement of the object in a same direction in which the needle is pointing over a predetermined threshold amount of time. In an embodiment, the threshold amount of time accounts for one or more pauses of the object in the tissue.

In an embodiment, block 320 can include one or more of blocks 320A through 320G in the following or other order.

At block 320A, selectively perform the dynamic ROI refinement by (i) shrinking the ROI so that a size of the ROI more accurately represents a location of the object in the tissue than before the dynamic ROI refinement is performed, and/or (2) advancing the ROI so that a position of the ROI more accurately represents an edge of interest of the object in the tissue than before the dynamic ROI refinement is performed.

At block 320B, constrain a maximum amount of shrinking of the ROI to a distance between the needle transducer and a tip of the needle.

At block 320C, determine an angle of advance of the ROI from a regressed slope of the object and the recorded path of movement of the object through the tissue.

At block 320D, determine an amount and direction of advancing the ROI (that is, the value D, as described herein) by extrapolating a path from the ultrasound transducer to the tip of the object.

At block 320E, maintain the dynamic ROI refinement when the object motion ceases for less than a threshold amount of time.

At block 320F, prevent or cease the dynamic ROI refinement from being performed responsive to a movement of the object in a different direction on the displayed image than the direction in which the object (the needle) is pointing. This off-track movement on the image may occur for instance when probe 288 is moved with respect to the object, such as when it is moved along the patient's skin, resulting in a lateral shift of the image. The calculated angle of advance of the object tip in block 320C will likewise increase or decrease as the recorded path of movement is affected by the probe 288 movement. This necessitates suppression of the dynamic ROI refinement until advancement in a substantially straight line is re-established, typically by advancing the object in isolation. The determination of the substantially straight line (via, preferably, position regression) is made initially at block 315 and may be refreshed at block 320C.

Similarly, at block 320G, deactivate the dynamic ROI refinement responsive to a change in a movement of the object to a different direction on the displayed image than the direction in which the needle is pointing.

Figure 5:
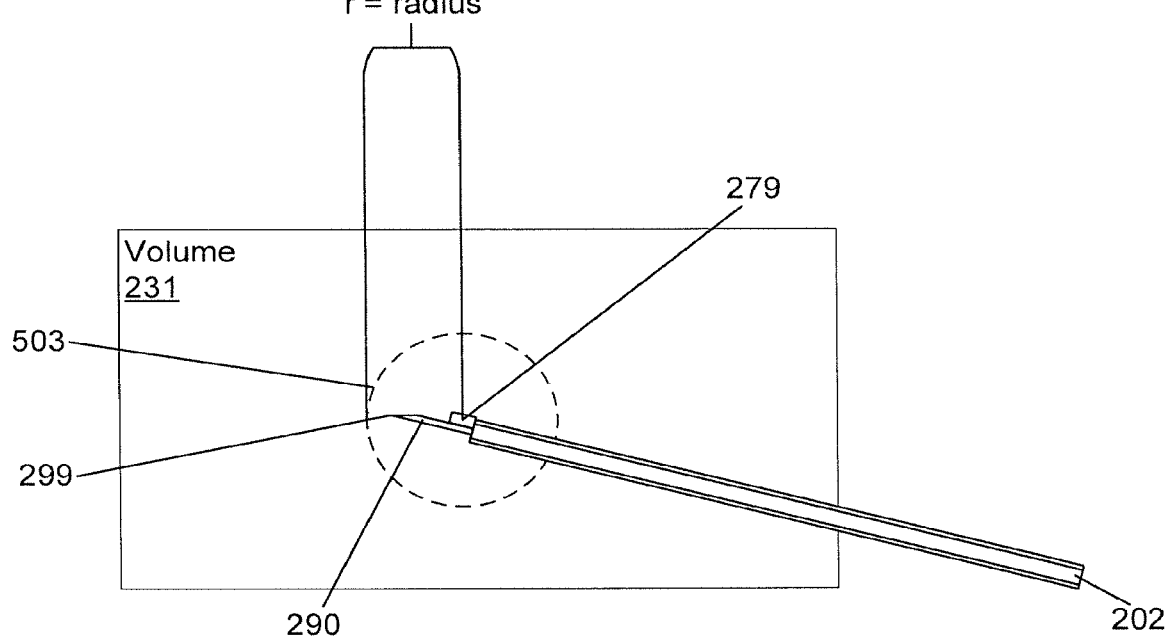
FIG. 5 is a diagram showing an object and Region Of Interest (ROI) corresponding to a non-refinement stage, in accordance with an embodiment of the present invention.
Figure 6:
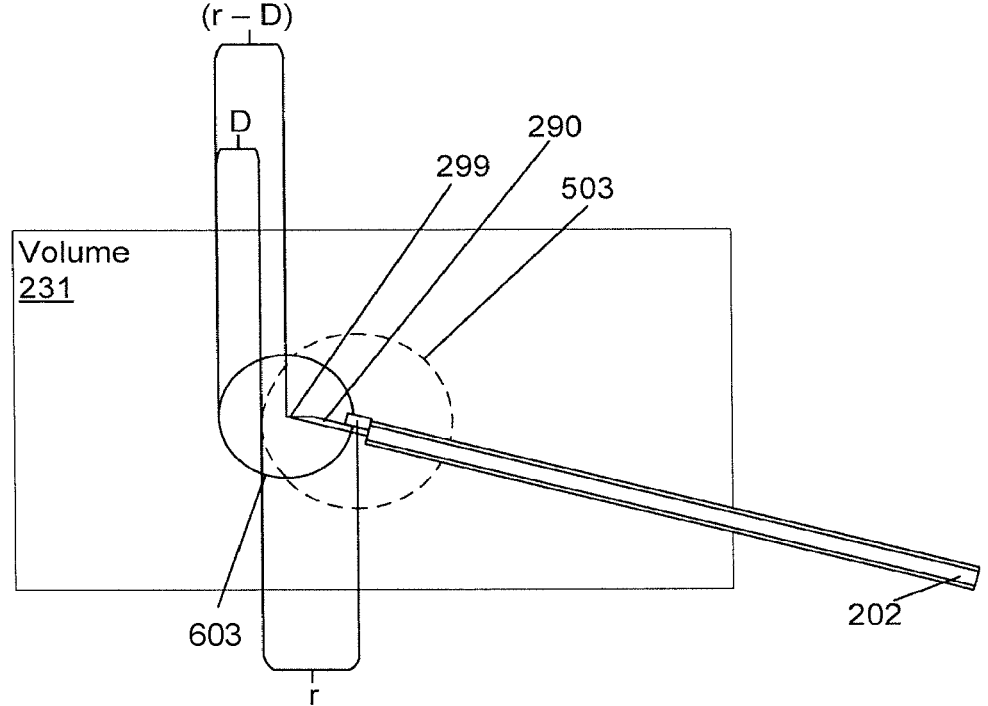
FIG. 6 is a diagram showing the object of FIG. 5 and a dynamically refined Region Of Interest (ROI) corresponding to a refinement stage, in accordance with an embodiment of the present invention.

FIGS. 5 and 6 respectively show an object and a corresponding ROI shape, corresponding to a non-refinement stage and a refinement stage applied to the ROI shape, in accordance with one or more embodiments of the present invention. It is to be appreciated that the elements in FIGS. 5 and 6 may not be drawn to scale, but are enumerated to show the relevant parameters.

FIG. 5 is a diagram showing an object (e.g., a needle) 290 and Region Of Interest (ROI) 503 corresponding to a non-refinement stage, in accordance with an embodiment of the present invention. In an embodiment, FIG. 5 can be considered to show an implementation of block 310 of method 300 of FIG. 3.

In an ultrasound system that tracks an object 290 by an ultrasound transducer 279 mounted near the tip 299 of the object 290, the location of the tip 299 of the object 290 is shown on the image by means of a small ROI/circle 503 that tracks the tip movement as the object 290 is advanced in the tissue. While the shown ROI is a circle, other shapes can be used. The center of the circle 503 is displayed by the system tracking algorithm at the physical location of the ultrasound transducer 279, and the radius r (before reduction by a value of D) of the circle 503 should be large enough to encompass the distance between the mounting location of the ultrasound transducer 279 and the end of the needle tip 299 itself, given the ambiguity of where the tip 299 is on the perimeter of the circle 503.

Hence, corresponding to a non-refinement stage of the present invention, ROI shape 503 encompasses the tip 299 at an unknown angle from the ultrasound transducer 279. As shown, the needle tip 299 is at the perimeter of the ROI shape 503, with the ROI shape 503 being centered on the ultrasound transducer 279 on the needle 290 (and not needle tip 299).

FIG. 6 is a diagram showing the object (e.g., needle 290) of FIG. 5 and a dynamically refined Region Of Interest (ROI) 603 corresponding to a refinement stage, in accordance with an embodiment of the present invention. In an embodiment, FIG. 6 can be considered to show an implementation of block 320 of method 300 of FIG. 3.

In the refinement stage, the tip 299 has advanced a few millimeters within circle 603, which is smaller than, and hence more precise, that circle 503 of FIG. 5 which is also shown in FIG. 6 for reference and comparisons sake. Thus, the present invention has both (i) reduced the size of the ROI shape 603 and (ii) advanced it over the needle tip 299, improving the accurate visualization of the needle tip 299. In an embodiment, the advancement of the circle is by a magnitude D, which is also the same amount of reduction of the radius (r) of the circle. That is, circle 503 has a radius r, and circle 603 has a radius (r–D), where D also denotes how much the circle has advanced in a direction of movement of the object. In an embodiment, the circle can be small enough that it does not even encompass the ultrasound transducer 279, depending upon the implementation. For example, in an embodiment, a user can select between various different maximum values of D by which the circle is (i) advanced and (ii) reduced in size. In this way, user control can be exhibited to control the parameters of the refinement to the ROI shape.

Figure 7:
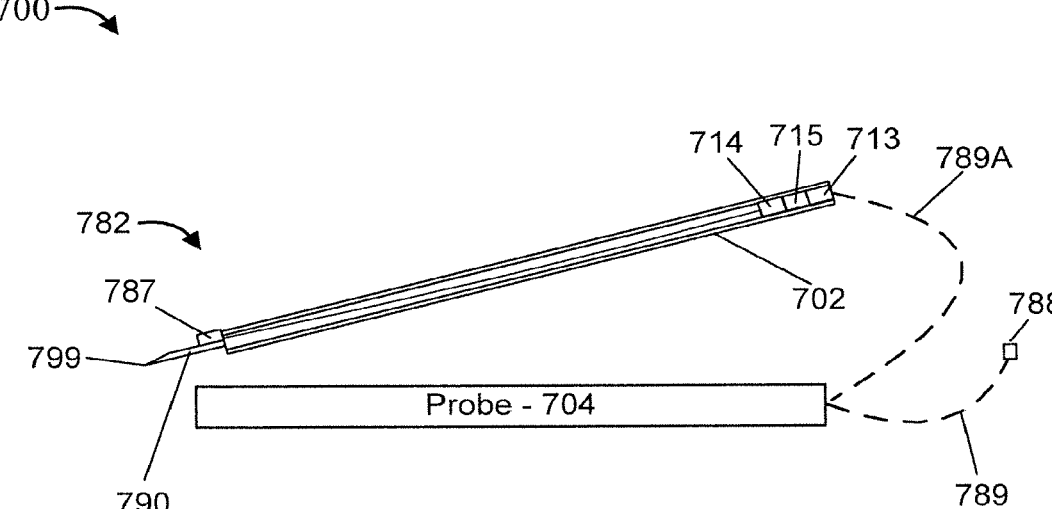
FIG. 7 is a block diagram showing another system 700 for ultrasound object point tracking, in accordance with an embodiment of the present invention.

FIG. 7 is a block diagram showing another system 700 for ultrasound object point tracking, in accordance with an embodiment of the present invention.

The system 700 includes an ultrasound probe 704 that cooperates with a medical instrument 702. The medical instrument 702 includes an ultrasound transducer 787 mounted on, e.g., a tip 799 of, the medical instrument 702.

The system 700 further includes a hardware processor 714, a memory 713, and a pulse detection module 715 which cooperate to render a Region Of Interest (ROI) relative to the tip on an ultrasound image displayed on a display device, and selectively perform a dynamic ROI refinement as the medical instrument is moved through the tissue to increase a location precision of the tip of the medical instrument in the ultrasound image. The dynamic ROI refinement is generated in accordance with physical characteristics of the medical instrument and a recorded path of movement of the medical instrument through the tissue. The hardware processor 714, memory 713, and pulse detection module 715 may be part of a circuit subsystem 782. Circuit subsystem 782 can include one or more elements of FIG. 2, depending upon the implementation, in order to obtain a compact system 700 relative to system 200. For example, while system 200 is envisioned in one embodiment being implemented using a cart specifically configured for use with system 200, in other embodiments, the ultrasound probe 704 can simply be connected to any display device. To that end, it is envisioned that circuit subsystem 782 at least includes ultrasound sensing module 215.

The medical instrument 702 may further include a catheter, a guidewire, a probe, an endoscope, a robot, an electrode, a filter device, a balloon device, or other medical component, etc. For the sake of illustration, medical instrument 702 includes a needle 790 having a tip 799. The preceding instruments are merely illustrative and, thus, other instruments can also be used with medical instrument 702.

Cabling 789 and connector (e.g., USB, etc.) 788 can be used to connect ultrasonic probe 704 to a display device and/or other elements. Cabling 789A can be used to connect ultrasonic probe 704 to medical instrument 702, in particular, pulse detection module 715. In other embodiments, wireless communication can be used.

In one example of the disclosure an ultrasound device for imaging an anatomical region, comprises: an ultrasound probe (288); a medical instrument (202) having an ultrasound transducer (279) mounted thereon; and a hardware processor (214) configured to render a Region Of Interest (ROI) relative to a distal end of the medical instrument on an ultrasound image displayed on a display device, and selectively perform a dynamic ROI refinement as the medical instrument (202) is moved through the anatomical region to increase a location precision of the distal end of the medical instrument (202) in the ultrasound image, the dynamic ROI refinement being generated in accordance with physical characteristics of the medical instrument and a recorded path of movement of the medical instrument through the anatomical region determined based on acoustic pulses transmitted between the ultrasound probe (288) and the ultrasound transducer (279). In this example the medical instrument (202) comprises a needle, and the dynamic ROI refinement is prevented from being performed responsive to a movement of the medical instrument in a different direction on the displayed image than a direction in which the needle is pointing.

In another example of the disclosure, in an ultrasound system that tracks a medical instrument in an anatomical region using an ultrasound transducer mounted on the medical instrument and displays a position of the medical instrument by rendering a Region Of Interest (ROI) relative to the distal end on an ultrasound image displayed on a display device, a method comprises: selectively performing (320) a dynamic ROI refinement as the medical instrument is moved through the anatomical region to increase a location precision of the distal end of the medical instrument in the ultrasound image, the dynamic ROI refinement being generated in accordance with physical characteristics of the medical instrument and a recorded path of movement of the medical instrument through the anatomical region.

It also should be understood that embodiments of the present invention will be described in terms of medical instruments; however, the teachings are much broader and are applicable to any ultrasound instruments. In some embodiments, the present principles are employed in tracking or analyzing devices in complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and digital video disc (DVD™).

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

In interpreting the appended claims, it should be understood that:

(a) the word "comprising" does not exclude the presence of other elements or acts than those listed in a given claim;

(b) the word "a" or "an" preceding an element does not exclude the presence of a plurality of such elements;

(c) any reference signs in the claims do not limit their scope;

(d) several "means" may be represented by the same item or hardware or software implemented structure or function; and (e) no specific sequence of acts is intended to be required unless specifically indicated.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Having described preferred embodiments of the present invention (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An ultrasound device for imaging an anatomical region in a person, comprising:
an ultrasound probe;
a medical instrument having an ultrasound transducer mounted on said medical instrument; and
a hardware processor configured to render a Region Of Interest (ROI) relative to a distal end of the medical instrument on an ultrasound image displayed on a display device, and selectively perform a dynamic ROI refinement as the medical instrument is moved through the anatomical region to increase a location precision of the distal end of the medical instrument in the ultrasound image, the dynamic ROI refinement being generated in accordance with physical characteristics of the medical instrument and a recorded path of movement of the medical instrument through the anatomical region determined by the hardware processor based on acoustic pulses transmitted between the ultrasound probe and the ultrasound transducer;
wherein the dynamic ROI refinement comprises advancing a position of the ROI on the ultrasound image based on the path of movement of the medical instrument in the anatomical region in the person so that the ROI on the ultrasound image remains centered around the distal end of the medical instrument as the medical instrument is moved through the anatomical region in the person.

2. The ultrasound device of claim 1, wherein the dynamic ROI refinement comprises shrinking the ROI so that a size of the ROI is smaller than before the dynamic ROI refinement is performed.

3. The ultrasound device of claim 1 wherein performing the dynamic ROI refinement comprises shrinking the ROI, and wherein the processor is configured to perform the dynamic ROI refinement by constraining a maximum amount of shrinking of the ROI to a distance between the ultrasound transducer and the distal end of the medical instrument.

4. The ultrasound device of claim 1 wherein an angle of advance of the ROI is determined from a regressed slope of the medical instrument and the recorded path of movement of the medical instrument through the anatomical region.

5. The ultrasound device of claim 1, wherein the refinement is maintained when the medical instrument motion ceases for less than a threshold amount of time.

6. The ultrasound device of claim 1, wherein the dynamic ROI refinement is selectively performed responsive to a direction of movement of the medical instrument.

7. The ultrasound device of claim 6, wherein the direction of movement is determined relative to a slope of the direction of movement of the medical instrument.

8. The ultrasound device of claim 1, wherein the medical instrument comprises a needle, and wherein the dynamic ROI refinement is only performed responsive to a movement of the medical instrument in a same direction in which the needle is pointing over a predetermined threshold amount of time.

9. The ultrasound device of claim 8, wherein the predetermined threshold amount of time accounts for one or more pauses of the medical instrument in the anatomical region.

10. The ultrasound device of claim 1, wherein the medical instrument comprises a needle, and wherein the dynamic ROI refinement is prevented from being performed responsive to a movement of the medical instrument in a different direction on the displayed image than a direction in which the needle is pointing.

11. The ultrasound device of claim 1, wherein the medical instrument comprises a needle, and wherein the dynamic ROI refinement is automatically deactivated responsive to a change in a movement of the medical instrument to a different direction on the displayed image than a direction in which the needle is pointing.

12. An ultrasound system for imaging an anatomical region in a person, comprising:
an ultrasound probe;
a medical instrument having an ultrasound transducer mounted on said medical instrument;
a display configured to display a position of the medical instrument by rendering a Region Of Interest (ROI) relative to a distal end of the medical instrument on an ultrasound image; and
a hardware processor configured to track the medical instrument in the anatomical region based on acoustic pulses transmitted between the ultrasound probe and the ultrasound transducer, and selectively perform a dynamic ROI refinement as the medical instrument is moved through the anatomical region to increase a location precision of the distal end of the medical instrument in the ultrasound image, the dynamic ROI refinement being generated in accordance with physical characteristics of the medical instrument and a recorded path of movement of the medical instrument through the anatomical region determined by the hardware processor based on the acoustic pulses transmitted between the ultrasound probe and the ultrasound transducer;
wherein the dynamic ROI refinement comprises advancing a position of the ROI on the ultrasound image based on the path of movement of the medical instrument in the anatomical region in the person so that the ROI on the ultrasound image remains centered around the distal end of the medical instrument as the medical instrument is moved through the anatomical region in the person.

13. The ultrasound system of claim 12, wherein the dynamic ROI refinement comprises shrinking the ROI so that a size of the ROI is smaller than before the dynamic ROI refinement is performed.

14. A method of tracking a medical instrument in an anatomical region in a person using an ultrasound transducer mounted on the medical instrument, the method comprising:

rendering a Region Of Interest (ROI) relative to the distal end on an ultrasound image to be displayed on a display device for displaying a position of the medical instrument;

selectively performing a dynamic ROI refinement as the medical instrument is moved through the anatomical region to increase a location precision of the distal end of the medical instrument in the ultrasound image, the dynamic ROI refinement being generated in accordance with physical characteristics of the medical instrument and a recorded path of movement of the medical instrument through the anatomical region, wherein the dynamic ROI refinement comprises advancing a position of the ROI on the ultrasound image based on the path of movement of the medical instrument in the anatomical region in the person so that the ROI on the ultrasound image remains centered around the distal end of the medical instrument as the medical instrument is moved through the anatomical region in the person; and displaying the ROI and the ultrasound image on the display device.

15. The method of claim 14, wherein the dynamic ROI refinement comprises shrinking the ROI so that a size of the ROI is smaller than before the dynamic ROI refinement is performed.

16. The method of claim 14 wherein performing the dynamic ROI refinement comprises shrinking the ROI, and wherein the processor is configured to perform the dynamic ROI refinement by constraining a maximum amount of shrinking of the ROI to a distance between the ultrasound transducer and the distal end of the medical instrument.

17. A computer-readable storage medium comprising program code for use by or in connection with a computer or any instruction execution system, the program code being configured for executing a method as claimed in claim 14.

* * * * *